US012758136B2

(12) United States Patent
Lohmeyer et al.

(10) Patent No.: US 12,758,136 B2
(45) Date of Patent: Oct. 13, 2026

(54) BEAT CLUSTERING

(71) Applicant: Boston Scientific Cardiac Diagnostics, Inc., Rochester, MN (US)

(72) Inventors: Drew Lohmeyer, Rochester, MN (US); Jan Hagenbrock, Rochester, MN (US); David R. Engebretsen, Cannon Falls, MN (US); Jeffrey R. Spors, Eyota, MN (US)

(73) Assignee: Boston Scientific Cardiac Diagnostics, Inc., Rochester, MN (US)

(*) Notice: Subject to any disclaimer, the term of this patent is extended or adjusted under 35 U.S.C. 154(b) by 296 days.

(21) Appl. No.: 18/655,920

(22) Filed: May 6, 2024

(65) Prior Publication Data

US 2024/0374195 A1 Nov. 14, 2024

Related U.S. Application Data

(60) Provisional application No. 63/464,651, filed on May 8, 2023.

(51) Int. Cl.

| | |
|---|---|
| ***A61B 5/339*** | (2021.01) |
| ***A61B 5/00*** | (2006.01) |
| ***A61B 5/346*** | (2021.01) |
| ***G16H 50/70*** | (2018.01) |

(52) U.S. Cl.
CPC .............. *A61B 5/339* (2021.01); *A61B 5/346* (2021.01); *A61B 5/7264* (2013.01); *G16H 50/70* (2018.01)

(58) Field of Classification Search
CPC ....... A61B 5/339; A61B 5/346; A61B 5/7264; A61B 5/0006; A61B 5/35; A61B 5/364; A61B 5/742; G16H 50/70
See application file for complete search history.

(56) References Cited

U.S. PATENT DOCUMENTS

| | | | | |
|---|---|---|---|---|
| 5,090,418 A * | 2/1992 | Squires | A61B 5/363 | 600/515 |
| 5,224,486 A * | 7/1993 | Lerman | A61B 5/339 | 600/509 |
| 2021/0298626 A1* | 9/2021 | Yu | A61B 5/346 | |
| 2024/0122521 A1* | 4/2024 | Hatano | A61B 5/349 | |

* cited by examiner

*Primary Examiner* — Eugene T Wu
(74) *Attorney, Agent, or Firm* — Faegre Drinker Biddle & Reath LLP

(57) ABSTRACT

A method includes displaying together plots of beats that are each associated with a first beat classification, selecting at least one of the plots of the beats to identify at least one selected beat, creating a subgroup of the beats based on a comparison of the beats associated with the first beat classification relative to the at least one selected beat, and reclassifying the beats in the subgroup to a second beat classification.

18 Claims, 7 Drawing Sheets

128

BEAT CLUSTERING

CROSS REFERENCE TO RELATED APPLICATION

This application claims priority to Provisional Application No. 63/464,651, filed May 8, 2023, which is herein incorporated by reference in its entirety.

TECHNICAL FIELD

The present disclosure relates to devices, methods, and systems for analyzing cardiac activity.

BACKGROUND

Monitoring devices for collecting biometric data are becoming increasingly common in diagnosing and treating medical conditions in patients. For example, mobile devices can be used to monitor cardiac data in a patient. This cardiac monitoring can empower physicians with valuable information regarding the occurrence and regularity of a variety of heart conditions and irregularities in patients. Classifying individual heartbeats can help accurately identify and classify cardiac events such as abnormal cardiac rhythms so that critical alerts can be provided to patients, physicians, or other care providers and patients can be treated.

SUMMARY

In Example 1, a method includes displaying together plots of beats that are each associated with a first beat classification; selecting at least one of the plots of the beats to identify at least one selected beat; creating a subgroup of the beats based on a comparison of the beats associated with the first beat classification relative to the at least one selected beat; and reclassifying the beats in the subgroup to a second beat classification.

In Example 2, the method of Example 1, wherein the comparison is based on latent space representations of the beats and the at least one selected beat.

In Example 3, the method of Example 2, wherein the latent space representations each include 4-16 datapoints for each beat.

In Example 4, the method of any of the preceding Examples, further including: calculating respective numerical values for the beats associated with the first classification, wherein the comparison includes comparing the respective numerical values to a threshold.

In Example 5, the method of Example 4, wherein the respective numerical values are calculated using a Euclidean distance algorithm.

In Example 6, the method of Example 5, wherein inputs to the Euclidean distance algorithm are values of the latent space representations.

In Example 7, the method of Examples 5 or 6, wherein the at least one selected beat comprises centroid values for the Euclidean distance algorithm.

In Example 8, the method of any of Examples 4-7, the method further including: increasing the threshold to increase the number of beats in the subgroup.

In Example 9, the method of any of the preceding Examples, wherein the displaying includes displaying together plots of beats in a first window on a user interface. The method further includes: extracting the plots of beats associated with the subgroup from the first window; and displaying the plots of beats associated with the subgroup in a second window.

In Example 10, the method of any of the preceding Examples, wherein the displaying includes displaying the plots of beats superimposed on each other.

In Example 11, the method of any of the preceding Examples, wherein the plots of the beats in the subgroup are displayed in a different color, line type, and/or line weight than the rest of the plots of the beats.

In Example 12, the method of any of the preceding Examples, wherein the first beat classification is a ventricular beat, wherein the second beat classification is a normal beat.

In Example 13, a computer program product includes instructions to cause one or more processors to carry out the steps of the method of Examples 1-12.

In Example 14, a computer-readable medium having stored thereon the computer program product of Example 13.

In Example 15, a computer comprising the computer-readable medium of Example 14.

In Example 16, a non-transitory computer-readable storage medium stores instructions, which-when executed on a processor-perform an operation. The operation includes causing plots of beats to be displayed together, where the plots of beats are each associated with a first beat classification and where the first beat classification is indicated by metadata associated with each beat. The operation further includes receiving a selection of at least one of the plots of the beats to identify a selected beat; creating a subgroup of the beats based on a comparison of the beats associated with the first beat classification relative to the selected beat; and reclassifying the beats in the subgroup to a second beat classification by updating the metadata associated with the beats in the subgroup.

In Example 17, the computer-readable storage medium of Example 16, wherein the comparison is based on latent space representations of the beats and the selected beat.

In Example 18, the computer-readable storage medium of Example 17, wherein the latent space representations each include 4-16 datapoints for each beat.

In Example 19, the computer-readable storage medium of Example 16, the operation further including: calculating respective numerical values for the beats associated with the first classification, wherein the comparison includes comparing the respective numerical values to a threshold.

In Example 20, the computer-readable storage medium of Example 19, wherein the respective numerical values are calculated using a Euclidean distance algorithm.

In Example 21, the computer-readable storage medium of Example 20, wherein inputs to the Euclidean distance algorithm are values of the latent space representations.

In Example 22, the computer-readable storage medium of Example 20, wherein the selected beat comprises centroid values for the Euclidean distance algorithm.

In Example 23, the computer-readable storage medium of Example 19, the operation further including: receiving a command to increase the threshold to increase the number of beats in the subgroup.

In Example 24, the computer-readable storage medium of Example 16, wherein the plots of beats are initially displayed together in a first window on a user interface, the operation further including: extracting the plots of beats associated with the subgroup from the first window; and causing the plots of beats associated with the subgroup to be displayed in a second window.

In Example 25, the computer-readable storage medium of Example 16, wherein the causing the plots of beats to be displayed together includes causing the plots of beats to be displayed superimposed on each other.

In Example 26, the computer-readable storage medium of Example 16, the operation further including: causing the plots of the beats in the subgroup to be displayed in a different color, line type, and/or line weight than the rest of the plots of the beats.

In Example 27, the computer-readable storage medium of Example 16, wherein the first beat classification is a ventricular beat, wherein the second beat classification is a normal beat.

In Example 28, a system includes a display for displaying a user interface, a processor, and a non-transitory computer-readable storage medium storing instructions. When executed by the processor, the instructions cause the processor to perform one or more operations, the one or more operations including: causing plots of beats to be displayed together on the user interface in a first window; receiving, from the user interface, a selection of at least one of the plots of the beats to identify a selected beat; calculating respective numerical values for the beats; and creating a subgroup of the beats based on a comparison of the beats relative to the selected beat. The comparison includes comparing the respective numerical values to a threshold. The one or more operations further include causing the plots of beats of the subgroup to be displayed together on the user interface in a second window.

In Example 29, the system of Example 28, the one or more operations further including reclassifying the beats in the subgroup to a second beat classification.

In Example 30, the system of Example 28, wherein the respective numerical values are calculated using a Euclidean distance algorithm.

In Example 31, the system of Example 28, wherein the calculating the respective numerical values for the beats does not include calculating a numerical value for the selected beat.

In Example 32, a method includes: displaying together plots of beats that are each associated with a first beat classification; selecting at least one of the plots of the beats to identify at least one selected beat; creating a subgroup of the beats based on a comparison of the beats associated with the first beat classification relative to the at least one selected beat; and reclassifying the beats in the subgroup to a second beat classification.

In Example 33, the method of Example 32, wherein the comparison is based on latent space representations of the beats and the at least one selected beat.

In Example 34, the method of Example 23, further including: calculating respective numerical values for the beats associated with the first classification, wherein the comparison includes comparing the respective numerical values to a threshold.

In Example 35, the method of Example 34, wherein the respective numerical values are calculated using a Euclidean distance algorithm.

While multiple instances are disclosed, still other instances of the present disclosure will become apparent to those skilled in the art from the following detailed description, which shows and describes illustrative instances of the disclosure. Accordingly, the drawings and detailed description are to be regarded as illustrative in nature and not restrictive.

Figure 1:
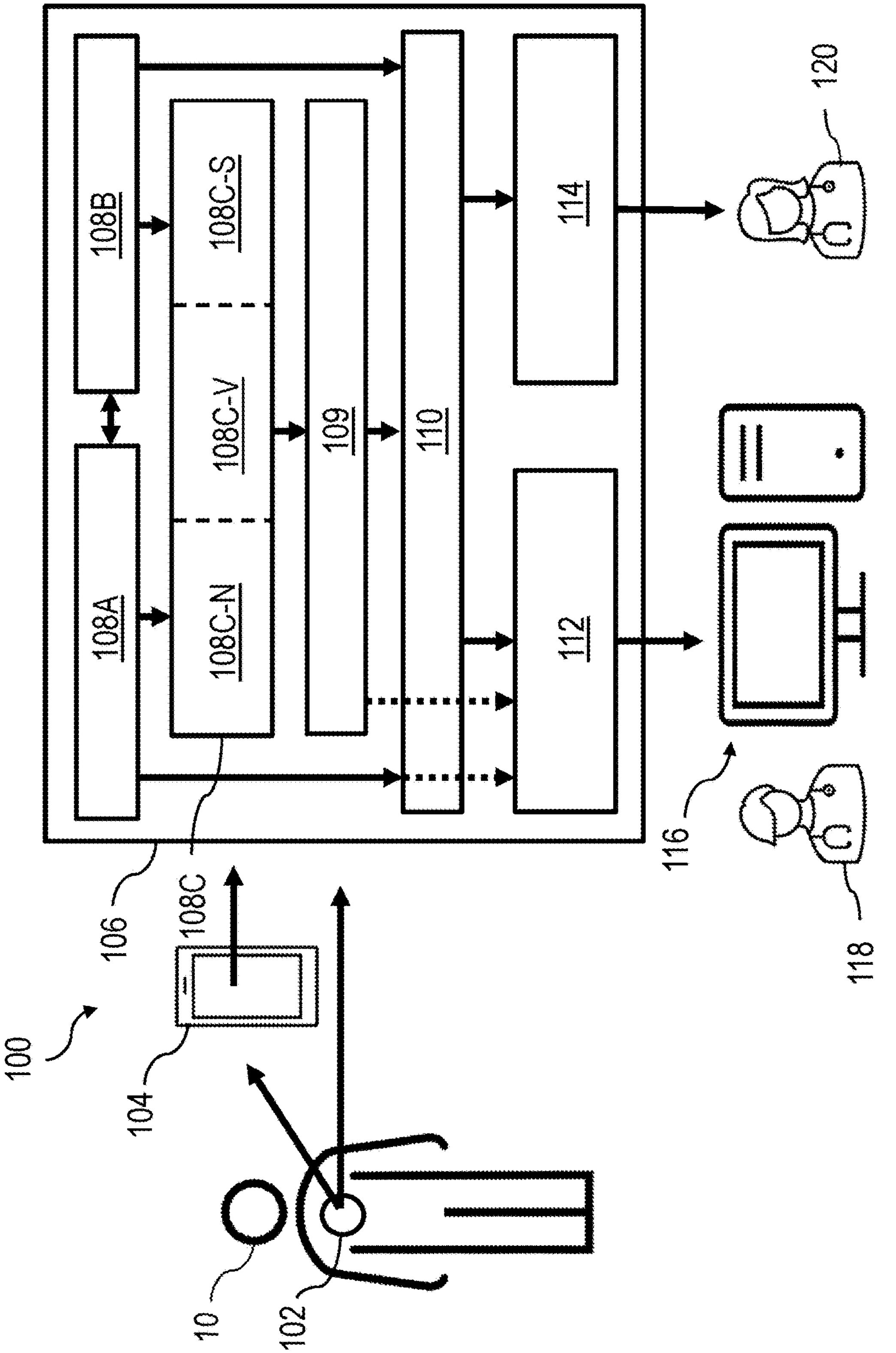
FIG. 1 shows a cardiac monitoring system, in accordance with certain instances of the present disclosure.

While the disclosed subject matter is amenable to various modifications and alternative forms, specific instances have been shown by way of example in the drawings and are described in detail below. The intention, however, is not to limit the disclosure to the particular instances described. On the contrary, the disclosure is intended to cover all modifications, equivalents, and alternatives falling within the scope of the disclosure as defined by the appended claims.

DETAILED DESCRIPTION

The present disclosure relates to devices, methods, and systems for classifying heartbeats (hereinafter "beats" for brevity) and grouping together similarly shaped beats in clusters. Such classification and clustering facilitate analysis of cardiac activity.

Electrocardiogram (ECG) data of a patient can be used to identify whether the patient has experienced a cardiac event and what type of cardiac event occurred. One input to determining the type of cardiac event includes the types (or classifications) of beats experienced during the cardiac event. For example, an ECG analysis system may automatically determine that a certain type of cardiac event occurred based on-among other things-how the system classified the beats occurring during the event. However, if the beats were initially misclassified, the determined type of cardiac event may also be misclassified and therefore may then need to be reevaluated. Instances of the present disclosure are accordingly directed to systems, methods, and devices for classifying and grouping beats and additionally for facilitating analysis and reclassification of beats.

FIG. 1 illustrates a patient 10 and an example system 100. The system 100 includes a monitor 102 attached to the patient 10 or implanted in the patient 10 (e.g., a pacemaker, ICD, CRT, or ICM) to detect cardiac activity of the patient 10. The monitor 102 may produce electric signals that represent the cardiac activity in the patient 10. For example, the monitor 102 may detect the patient's heart beating (e.g., using infrared sensors, electrodes, heart sounds) and convert the detected heartbeat into electric signals representing ECG data. In certain instances, the monitor 102 stores the ECG data of a patient study (e.g., one or more days of ECG data), after which the ECG data is transmitted to another device or system such as a server. Additionally or alternatively, the monitor 102 transmits the ECG data to a mobile device 104 (e.g., a mobile phone). In such instances, the mobile device 104 can include a program (e.g., mobile phone application) that receives, processes, and analyzes the ECG data. For example, the program may analyze the ECG data and detect or flag cardiac events (e.g., periods of irregular cardiac activity) contained within the ECG data. The mobile device 104 can periodically transmit chunks of the ECG data to another device or system such as a server, which can process, append together, and archive the chunks of the ECG data and metadata (e.g., time, duration, detected/flagged cardiac events) associated with the chunks of ECG data. In certain instances, the monitor 102 may be programmed to transmit the ECG data directly to the other device or system without utilizing the mobile device 104. Also, the monitor 102 and/or the mobile device 104 includes a button or touch-screen icon that allows the patient 10 to initiate an event. Such an indication can be recorded and communicated to the other device or system. In other instances involving multi-day studies, the ECG data and associated metadata are transmitted in larger chunks (e.g., an entire study's worth of ECG data).

Cardiac Event Server

The ECG data (and associated metadata, if any) is transmitted to and stored by a cardiac event server 106 (hereinafter "the server 106" for brevity). The server 106 includes multiple models, platforms, layers, or modules that work together to process and analyze the ECG data such that cardiac events can be detected, filtered, prioritized, and ultimately reported to a patient's physician for analysis and treatment. In the example of FIG. 1, the server 106 includes one or more machine learning models 108A, 108B, and 108C, a clustering algorithm module 109, a cardiac event router 110, a report platform 112, and a notification platform 114. Although only one server 106 is shown in FIG. 1, the server 106 can include multiple separate physical servers, and the various models/platforms/modules/layers can be distributed among the multiple servers. Each of the models/platforms/modules/layers can represent separate programs, applications, and/or blocks of code where the output of one of the models/platforms/modules/layers is an input to another of the models/platforms/modules/layers. Each of the models/platforms/modules/layers can use application programming interfaces to communicate between or among the other models/platforms/modules/layers as well as systems and devices external to the server 106.

In certain instances, once the ECG data is processed by the machine learning models 108A-C and the clustering algorithm module 109, the ECG data (and associated metadata) is made available for the report platform 112. As will be described in more detail below, the report platform 112 can be accessed by a remote computer 116 (e.g., client device such as a laptop, mobile phone, desktop computer, and the like) by a user at a clinic or lab 118. In other instances, the cardiac event router 110 is used to determine what platform further processes the ECG data based on the classification associated with the cardiac event. For example, if the identified cardiac event is critical or severe, the cardiac event router 110 can flag or send the ECG data, etc., to the notification platform 114. The notification platform 114 can be programmed to send notifications (along with relevant ECG data and associated metadata) immediately to the patient's physician/care group remote computer 116 and/or to the patient 10 (e.g., to their computer system, e-mail, mobile phone application).

Figure 2:
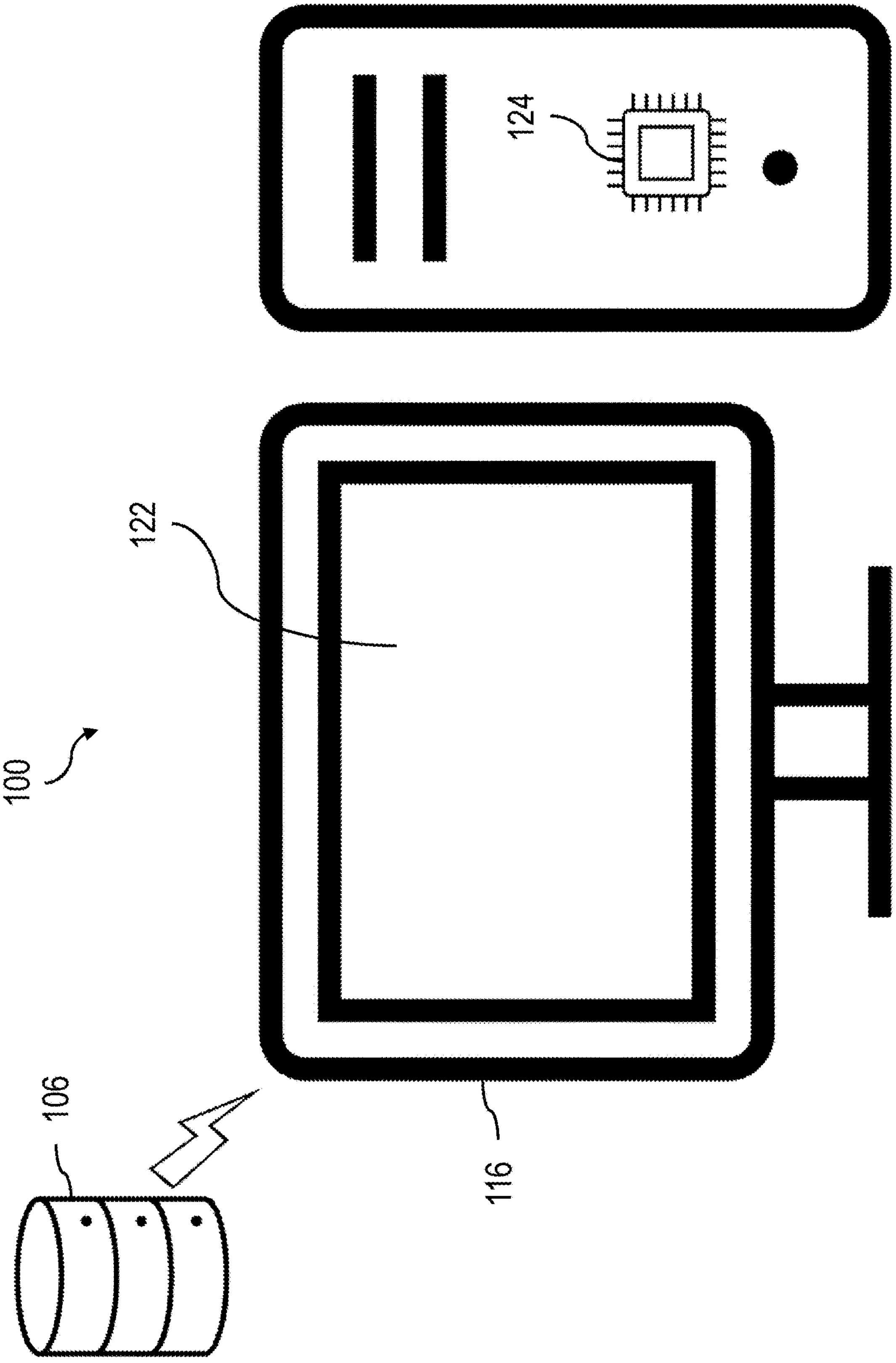
FIG. 2 shows a server, a remote computer, and a user interface, in accordance with certain instances of the present disclosure.

FIG. 2 shows the server 106 communicatively coupled (e.g., via a network) to the remote computer 116. In the example of FIG. 2, the remote computer 116 includes a monitor showing a user interface 122 (hereinafter "the UI 122" for brevity) that displays features of the report platform 112 hosted by the server 106. The UI 122 includes multiple pages or screens for tracking and facilitating analysis of patient ECG data.

In certain instances, the report platform 112 is a software-as-a-service (SaaS) platform hosted by the server 106. To access the report platform 112, a user (e.g., a technician) interacts with the UI 122 to log into the report platform 112 via a web browser such that the user can use and interact with the report platform 112.

Machine Learning Models

The server 106 applies the one or more machine learning models 108A-C to the ECG data to analyze and classify the beats and cardiac activity of the patient 10.

As described in more detail below, the first and second machine learning models 108A and 108B are programmed to—among other things—compare the ECG data to labeled ECG data to determine which labeled ECG data the ECG data most closely resembles. The labeled ECG data may identify a particular cardiac event—including but not limited to ventricular tachycardia, bradycardia, atrial fibrillation, pause, normal sinus rhythm, or artifact/noise—as well as particular beat classifications—including but not limited to ventricular, normal, or supraventricular. In addition to identifying beat classifications and event classifications (and generating associated metadata), the first and second machine learning models 108A and 108B can determine and generate metadata regarding heart rates, duration, and beat counts of the patient 10 based on the ECG data. As specific examples, the first and/or the second machine learning models 108A and 108B can identify the beginning, center, and end of individual beats (e.g., individual T-waves) such that individual beats can be extracted from the ECG data. Each individual beat can be assigned a value (e.g., a unique identifier) such that individual beats can be identified and associated with metadata throughout processing and analyzing the ECG data.

The ECG data (e.g., ECG data associated with individual beats) as well as certain outputs of the first and second machine learning models 108A and 108B can be inputted to the third machine learning model 108C. Although two machine learning models are shown and described, a single machine learning model could be used to generate the metadata described herein, or additional machine learning models could be used.

The first and second machine learning models 108A and 108B can include the neural networks described in Ser. No. 16/695,534, which is hereby incorporated by reference in its entirety. The first neural network can be a deep convolutional neural network and the second neural network is a deep fully-connected neural network—although other types and combinations of machine learning models can be implemented. The first machine learning model 108A receives one or more sets of beats (e.g., beat trains with 3-10 beats) which are processed through a series of layers in the deep convolutional neural network. The series of layers can include a convolution layer to perform convolution on time series data in the beat trains, a batch normalization layer to normalize the output from the convolution layer (e.g., centering the results around an origin), and a non-linear activation function layer to receive the normalized values from the batch normalization layer. The beat trains then pass through a repeating set of layers such as another convolution layer, a batch normalization layer, a non-linear activation function layer. This set of layers can be repeated multiple times.

The second machine learning model 108B receives RR-interval data (e.g., time intervals between adjacent beats) and processes the RR-interval data through a series of layers: a fully connected layer, a non-linear activation function layer, another fully connected layer, another non-linear activation function layer, and a regularization layer. The output from the two paths is then provided to the fully connected layer. The resulting values are passed through a fully connected layer and a softmax layer to produce probability distributions for the classes of beats.

The third machine learning model 108C (e.g., one or more trained encoder machine learning models) is programmed to generate latent space representations of the ECG data such that the ECG data is represented by fewer datapoints than the original ECG data. The latent space representations can be used as an approximation of the original raw ECG data for each beat. Although the inputs to the third machine learning model 108C are described as (1) the ECG data such as sets of individual T-waves and (2) certain outputs of the first and second machine learning models 108A and 108B, the third machine learning model 108C could be programmed to generate the latent space representations without requiring input from the first and/or second machine learning models 108A, 108B.

In certain instances, instead of a single third machine learning model 108C, the server 106 includes a separate machine learning model for each type of beat classification (e.g., normal beats, ventricular beats, and supraventricular beats). For example, as shown in FIG. 1, the server 106 may include three third machine learning models (108C-N, 108C-V, and 108C-S) instead of a single third machine learning model. In certain instances, beats that were not initially classified (e.g., unclassified beats) can be processed either by a different third machine learning model or can skip the step of generating latent space representations and being clustered with similar shaped beats.

In the example of FIG. 1, one machine learning model 108C-N is used for beats classified as normal beats, another machine learning model 108C-V is used for beats classified as ventricular beats, and another machine learning model 108C-S is used for beats classified as supraventricular beats. As such, only ECG data (e.g., T-waves) of beats initially classified as normal beats by the first and/or second machine learning models 108A, 108B—as well as metadata generated by such machine learning models—are inputted to the machine learning model 108C-N, and so on. It has been found that using machine learning models trained to focus on analyzing only certain types of beats can improve performance of the third machine learning models compared to using a single third machine learning model. Further, processing the ECG data in parallel using three machine learning models can decrease the time needed to generate the latent space representations. In certain instances, a single study may contain hundreds of thousands to millions of individual beats.

Each third machine learning model (108C-N, 108C-V, 108C-S) receives ECG data associated with individual beats (e.g., an individual clip of ECG data for each beat) and generates latent space representations of such ECG data. For example, each individual beat is processed by one of the third machine learning models-depending on each individual beat's classification—such that the ECG data is distilled down to (or represented by) a small number of individual data points. Raw ECG data of an individual beat can include 500 or so datapoints, and each third machine learning model can distill the ECG data for a given beat into 4-16 datapoints. Put another way, each third machine learning model can generate latent space representations comprising 4-16 datapoints for a given beat. This range has been found to balance accuracy of beat representation and effectiveness of clustering (described further below). In certain instances, the latent space representations comprise 7, 8, or 9 (e.g., 7-9) datapoints for a given beat. The latent space representations comprise 1-2% of datapoints compared to the raw ECG data for each beat. Each latent space can be represented by a vector (e.g., a latent vector).

Figure 3:
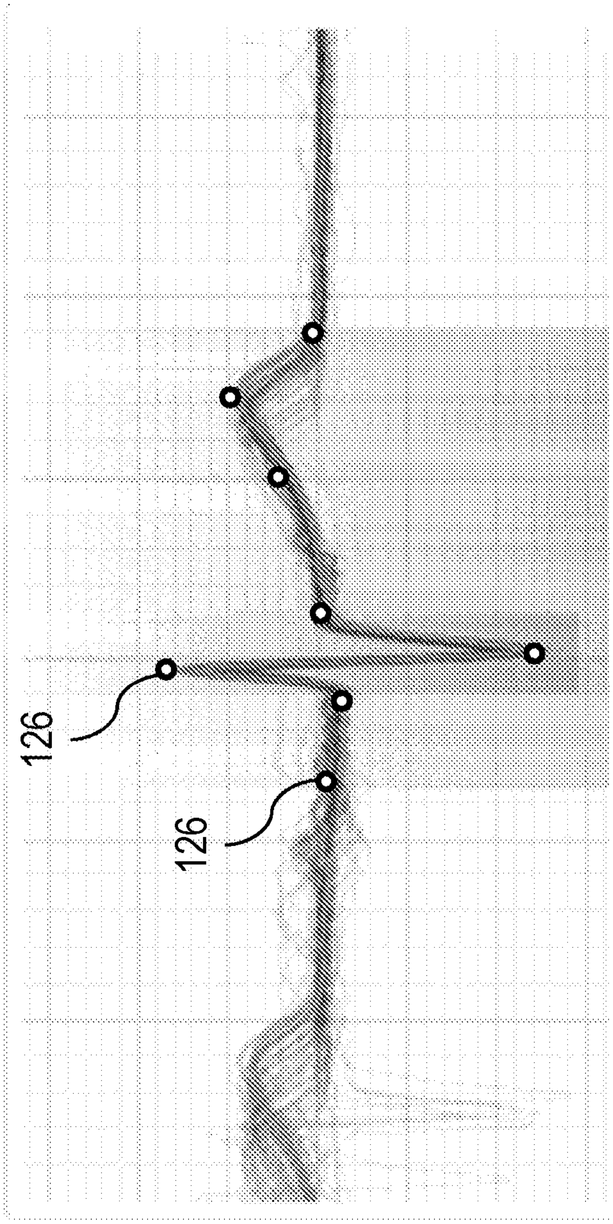
FIG. 3 shows an example of beats that have been grouped together and displayed in a user interface, in accordance with certain instances of the present disclosure.

The resulting datapoints are representations of an amplitude of the ECG signal at different relative points in time. These limited datapoints are datapoints that the trained machine learning models generate such that different beat shapes can be identified and similar shaped beats can be grouped together. Put another way, these datapoints may be those that are the most likely to be helpful in distinguishing among beat shapes. The third machine learning models can leave out representations of datapoints that are less likely to help distinguish among individual beats. FIG. 3 shows an example set of beats that have been grouped or clustered together and also shows non-limiting examples of points 126 within a beat's ECG signal that may be useful for distinguishing among beat shapes. For example, the points 126 can be located at the beginning and end of each beat, apexes (e.g., QRS peak), nadirs, etc.

In the example of FIG. 1, the third machine learning models (108C-N, 108C-V, 108C-S) generate respective separate latent space representations for sets of beats initially classified as normal beats, ventricular beats, and supraventricular beats. In certain instances, beats that could not be initially classified (or ECG data containing artifacts due to noise) are not processed by any of the third machine learning models. Such beats can be labeled as unclassified beats.

The output(s) of the third machine learning model(s) 108C are processed by a clustering algorithm module 109. The clustering algorithm module 109 receives the latent space representations of individual beats and is programmed to associate similar shaped beats into different groups. FIG. 3 shows an example set of beats that have been grouped or clustered together. As shown in FIG. 3, ECG waveforms of individual beats (e.g., T-waves) are superimposed on each other. Each cluster or group can include hundreds or thousands of beats that have been grouped together by the clustering algorithm module 109. As can be seen, the beats all have a similar profile relative to each other. Each beat is aligned with the other beats to have respective QRS peaks centered on the graph.

In certain instances, the clustering algorithm module 109 is programmed to apply a clustering algorithm such as the k-means clustering algorithm or a derivation or variation thereof to the latent space representations. In certain instances, the same clustering algorithm module 109 and the same algorithm is used to process the latent space representations of each of the third machine learning models (108C-N, 108C-V, 108C-S). In certain instances, the output of the clustering algorithm module 109 includes assigning a value (e.g., an identifier such as a number) to each beat that is indicative of the group selected by the clustering algorithm module 109. For example, if the clustering algorithm module 109 clusters the beats into eight different groups, then all beats selected to be in the first group may be assigned a value of "1" and all beats selected to be in the second group may be assigned a value of "2" and so on. Other types of values can be used. These group values can be added to the metadata associated with each beat.

The groups of beats are ultimately presented to an end user in an ECG analysis tool and used for efficient review of a large amount of ECG data (e.g., one or more days of ECG data). The server 106 (e.g., via programming associated with the report platform 112) can start a process for sending data to the remote computer 116. This data includes the ECG data and metadata (e.g., beat classifications) associated with the ECG data. The initial packages of data can include: (1) short strips of ECG data that include and surround detected cardiac events, (2) metadata associated with the strips, and (3) executable code (e.g., JavaScript code).

Beat Analysis

Figure 4:
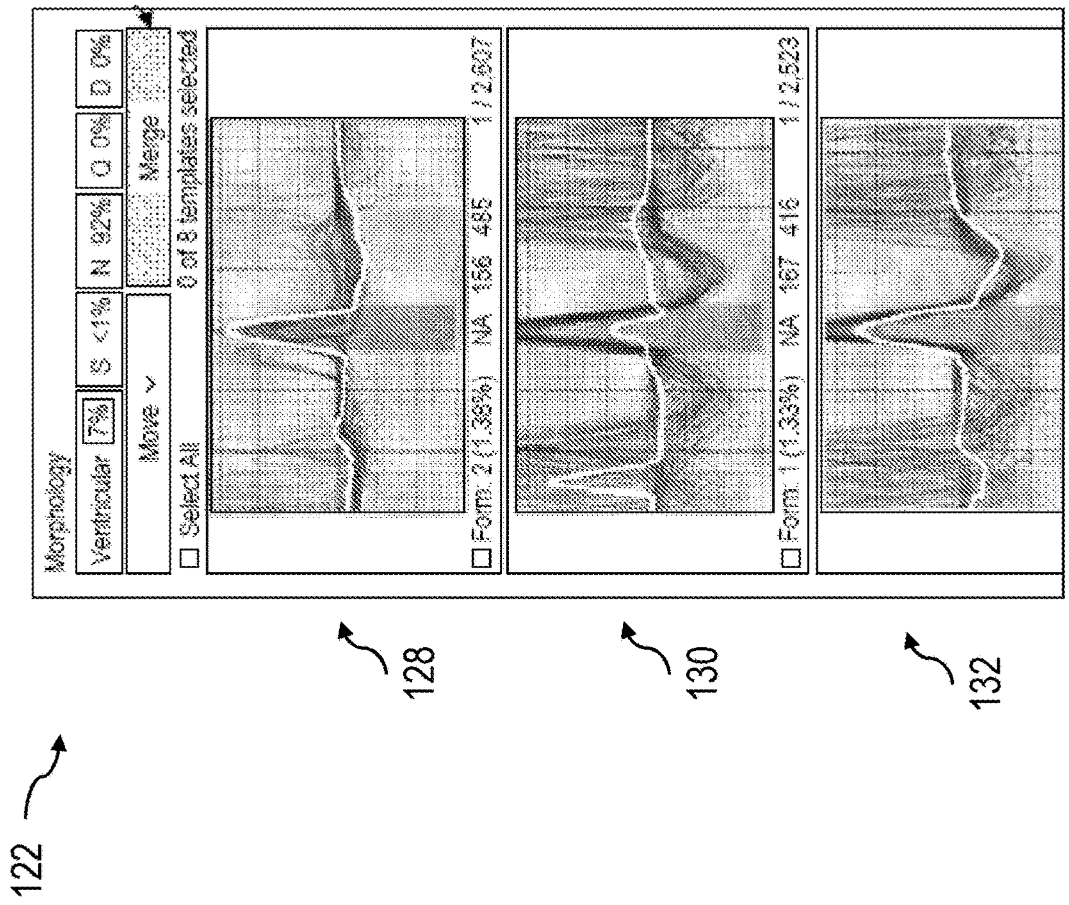
FIGS. 4 and 5 show additional plots of beats that have been grouped together, in accordance with certain instances of the present disclosure.

In FIG. 4, the UI 122 is shown displaying together plots of ECG data in various windows 128, 130, and 132. Each window can display multiple plots of beat-sized strips of ECG data that have been similarly classified (e.g., by the clustering algorithm module 109). For example, the plots of beats in the first window 128 can be associated with a first beat classification while the plots of beats in the second window 130 can be associated with a different beat classification, and so on. Example beat classifications include normal beats, ventricular beats, supraventricular beats, and unknown beats.

As shown, each window 128, 130, 132 includes multiple plots that are superimposed on each other. Each window can display plots of hundreds or more of beats that have been grouped together by the autoencoder DNN. In certain instances, the windows show only a subset of available plots for beats that have been grouped together. For example, one group may contain thousands of beats, but only a representative number (e.g., 100-300 beats, 150-250 beats, 190-210 beats) of plots are displayed in the windows for easier viewing. Each beat can be aligned to have its QRS peak centered on the graph so that the beats can be visually compared to each other. The plots of beats in each separate window generally have similar profiles to each other.

However, the groups of beats can contain subgroups of beats that should be separately classified, that are errant, and/or that otherwise should be extracted/removed from the larger group. The following paragraphs in this section describe approaches for identifying and addressing such subgroups of beats.

Figure 5:
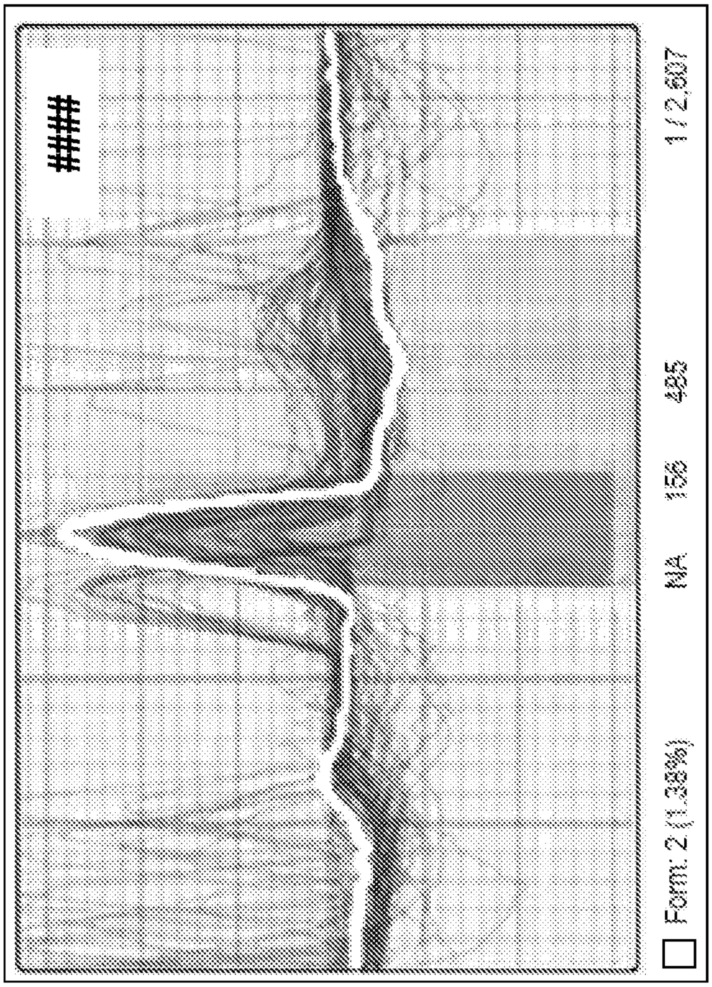
Figure 6:
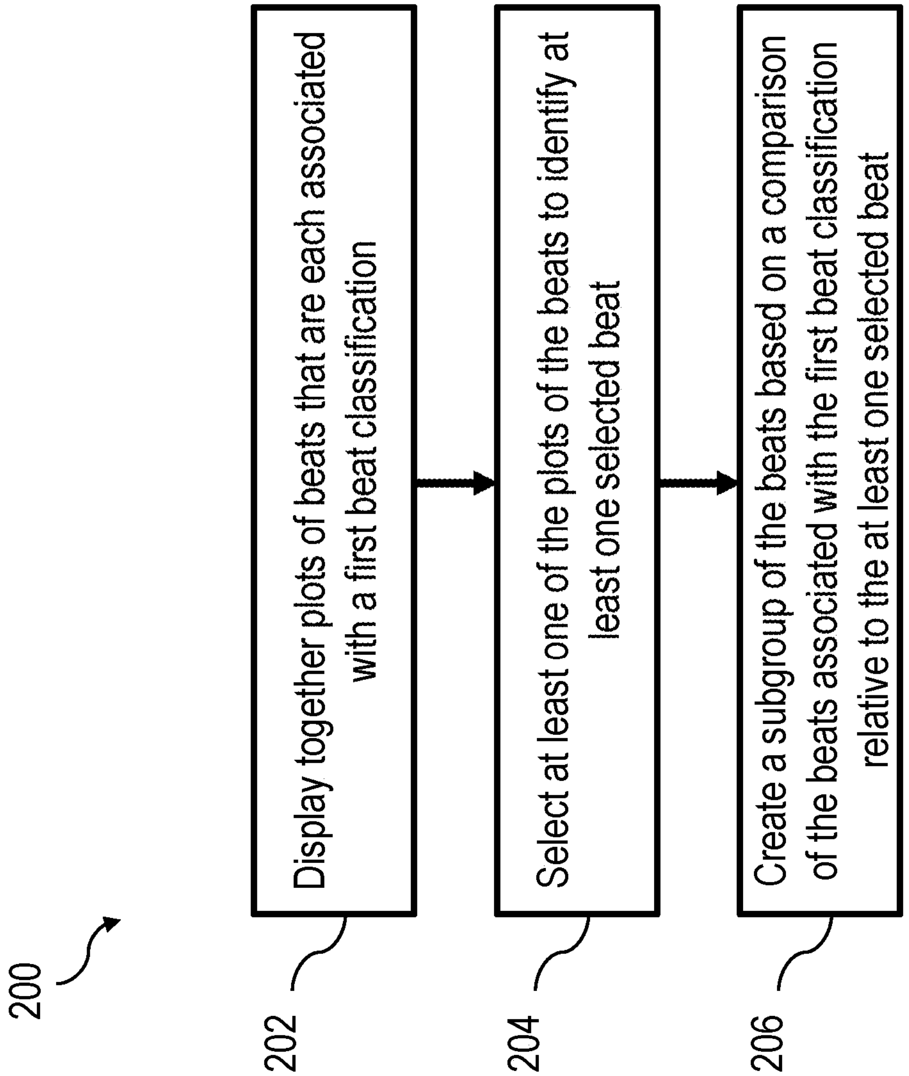
FIG. 6 shows a block diagram depicting an illustrative method, in accordance with certain instances of the disclosure.

FIG. 5 shows one of the windows 128 of the UI 122, and FIG. 6 shows an outline of steps of a method 200 for analyzing beats. The method 200 includes displaying—in the window 128—plots of beats that are each associated with a first beat classification (block 202 of FIG. 6).

The method 200 also includes selecting at least one of the plots of the beats in the window 128 to identify at least one selected beat (block 204 of FIG. 6). For example, a user can use a displayed cursor (controlled by a mouse, keyboard, etc.) to select a plot that is displayed in the window 128. Once a plot is selected, the selected plot(s) can be displayed in a different color, line weight, and/or line type than the rest of the plots in the window 128. In the example in FIG. 5, the selected plot(s) are shown in white whereas the unselected plots are shown in black. As noted above, a plot may be selected because the plot should be separately classified, is errant, and/or that otherwise should be extracted/removed from the larger group.

The selected plot can be used to identify other plots of beats that are similar to the selected plot. For example, the method 200 can include creating a subgroup of beats that have plots similar to the selected plot. Creating the subgroup can be based on a comparison of the selected beat with the rest of the beats associated with the window 128 (block 206 in FIG. 6).

In certain instances, the comparison between the selected beat and the other beats involves calculating a numerical value for each beat that indicates the similarity (or dissimilarity) each beat has relative to the selected beat. For example, the numerical value can be based on a comparison of the distance between the latent space representations of the plot of the selected beat to those of the other individual beats associated with the window 128. The calculated numerical values can be compared to a threshold, and any beat associated with a numerical value that is within the threshold can be included in the subgroup.

As one example, the numerical values can be calculated using a Euclidean distance algorithm (see Equation 1 below). The inputs to the Euclidean distance algorithm can be values of the latent space representations, which were described above. Such values can be compared to the latent space representations of the plot of the selected beat-which can be considered centroid values for the Euclidean distance algorithm. For example, if each beat is associated with eight latent space representations, the calculated numerical value would be based, at least in part, on the difference between each's beat eight latent space representations and those of the selected beat. The "distance" for beats with similar shapes to the selected beat will have a smaller distance numerical value than dissimilar shapes.

$$\text{distance} = \sqrt{\sum_{i=0}^{n} (x_i - y_i)^2} \qquad \text{Equation 1}$$

A "distance" for each beat can be calculated and compared to a distance threshold value. In certain instances, a distance numerical value is not calculated for the selected beat because the distance would zero. In certain instances, the threshold value can be adjusted. For example, a user can increase the threshold value such that the number of beats in the subgroup increases or decrease the threshold value such that the number of beats in the subgroup decreases. The threshold value can be adjusted using an input device such as a keyboard (e.g., using predefined or custom hotkeys), a mouse, and the like.

As noted above, the window 128 may only display a subset of plots of beats that were initially grouped together. As such, beats may be included in the subgroup-based on the comparison described above-regardless of whether their plots are displayed in the window 128. For the plots that are displayed in the window 128, the plots of beats that are included in the subgroup can be displayed in a different color, line weight, and/or line type than the rest of the plots in the window 128. The window 128 can include a numerical indicator that displays the number or percentage of beats in the subgroup. As the threshold is adjusted, the numerical indicator can adjust as additional or fewer beats are included in the subgroup.

Once the threshold value is selected to establish the desired subgroup, the beats included in the subgroup can be extracted from the rest of the beats. For example, the user can create a new, second window in which the plots of the beats of the subgroup are displayed. Alternatively, the user can merge the subgroup of beats with beats of an already-existing window.

Additionally, the beats can be reclassified to a different beat classification. For example, a user can select all beats in the subgroup and make a mass update to the beats' metadata. Metadata for hundreds to thousands to hundreds of thousands (or millions, for long studies) of beats can be updated en masse through the UI. Because a set of ECG data may represent tens of thousands, hundreds of thousands, or even millions of individual beats, this ability to make mass updates to beats saves the user time in analyzing ECG data and, ultimately, building a report.

To save processing and network resources and to allow these changes to metadata to occur in real-time, the calculations and changes to the cardiac event classifications and the automatic updates to the beat classifications can be carried out locally on the remote computer 116—as opposed to sending data back and forth between the server 106 and the remote computer 116. For example, the reclassifications can be carried out using cache memory 124 (shown in FIG. 2) and processing capabilities (e.g., one or more microprocessors) of the remote computer 116. To enable local processing and updating, the report platform 112 can send the remote computer 116 code to execute locally. This code uses (or operates on) the outputs of the machine learning model 108 such as the beat classifications and rhythm classifications (as opposed to the underlying or raw ECG data), which reduces the computational resources needed to process the changes made by user locally at the remote computer 116. In certain embodiments, this code is executed by an internet browser operating on the remote computer 116.

In certain instances, once a final report is built and complete, the remote computer 116 can send any changes to the metadata (e.g., the subsequent beat classifications and subsequent rhythm classifications) to the server 106 and its database. The server 106 can then replace the metadata initially created by the machine learning model (and saved to the database) with the metadata generated by the remote computer 116 while the user was reviewing and editing the metadata. As such, if the ECG and metadata need to be accessed again, the server's database has the most recent version of the metadata. Further, the machine learning models 108 may be further trained on the metadata generated by the user at the remote computer 116.

Computing Devices and Systems

Figure 7:
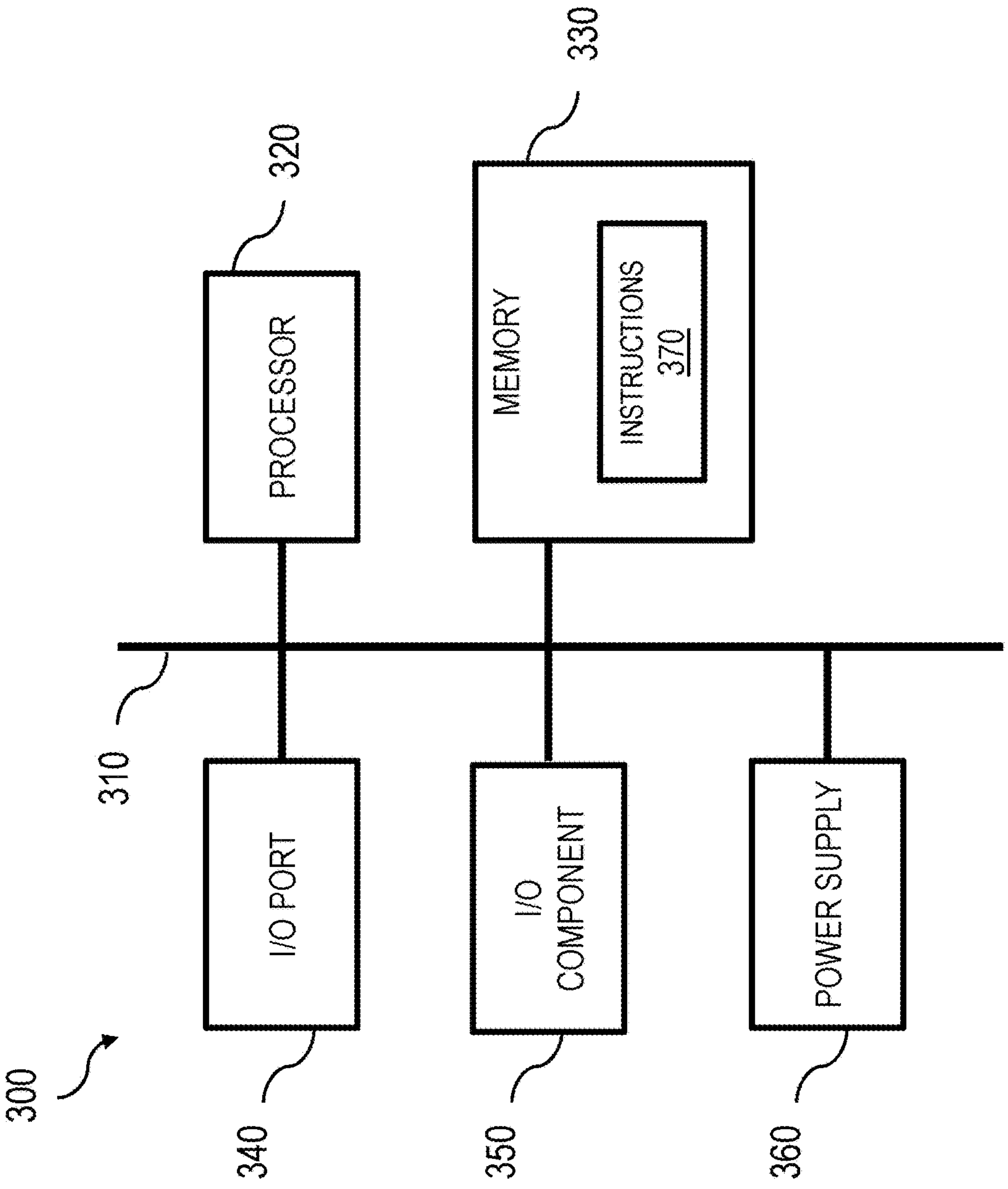
FIG. 7 is a block diagram depicting an illustrative computing device, in accordance with instances of the disclosure.

FIG. 7 is a block diagram depicting an illustrative computing device 300, in accordance with instances of the disclosure. The computing device 300 may include any type of computing device suitable for implementing aspects of instances of the disclosed subject matter. Examples of computing devices include specialized computing devices or general-purpose computing devices such as workstations, servers, laptops, desktops, tablet computers, hand-held devices, smartphones, general-purpose graphics processing units (GPGPUs), and the like. Each of the various components shown and described in the Figures can contain their own dedicated set of computing device components shown in FIG. 7 and described below. For example, the mobile device 104, the server 106, and the remote computer 116 can each include their own set of components shown in FIG. 7 and described below.

In instances, the computing device 300 includes a bus 310 that, directly and/or indirectly, couples one or more of the following devices: a processor 320, a memory 330, an input/output (I/O) port 340, an I/O component 350, and a power supply 360. Any number of additional components, different components, and/or combinations of components may also be included in the computing device 300.

The bus 310 represents what may be one or more busses (such as, for example, an address bus, data bus, or combination thereof). Similarly, in instances, the computing device 300 may include a number of processors 320, a number of memory components 330, a number of I/O ports 340, a number of I/O components 350, and/or a number of power supplies 360. Additionally, any number of these components, or combinations thereof, may be distributed and/or duplicated across a number of computing devices.

In instances, the memory 330 includes computer-readable media in the form of volatile and/or nonvolatile memory and may be removable, nonremovable, or a combination thereof. Media examples include random access memory (RAM); read only memory (ROM); electronically erasable programmable read only memory (EEPROM); flash memory; optical or holographic media; magnetic cassettes, magnetic tape, magnetic disk storage or other magnetic storage devices; data transmissions; and/or any other medium that can be used to store information and can be accessed by a computing device. In instances, the memory 330 stores computer-executable instructions 370 for causing the processor 320 to implement aspects of instances of components discussed herein and/or to perform aspects of instances of methods and procedures discussed herein. The memory 330 can comprise a non-transitory computer readable medium storing the computer-executable instructions 370.

The computer-executable instructions 370 may include, for example, computer code, machine-useable instructions, and the like such as, for example, program components capable of being executed by one or more processors 320 (e.g., microprocessors) associated with the computing device 300. Program components may be programmed using any number of different programming environments, including various languages, development kits, frameworks, and/or the like. Some or all of the functionality contemplated herein may also, or alternatively, be implemented in hardware and/or firmware.

According to instances, for example, the instructions 370 may be configured to be executed by the processor 320 and, upon execution, to cause the processor 320 to perform certain processes. In certain instances, the processor 320, memory 330, and instructions 370 are part of a controller such as an application specific integrated circuit (ASIC), field-programmable gate array (FPGA), and/or the like. Such devices can be used to carry out the functions and steps described herein.

The I/O component 350 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The devices and systems described herein can be communicatively coupled via a network, which may include a local area network (LAN), a wide area network (WAN), a cellular data network, via the internet using an internet service provider, and the like.

Aspects of the present disclosure are described with reference to flowchart illustrations and/or block diagrams of methods, devices, systems and computer program products. It will be understood that each block of the flowchart illustrations and/or block diagrams, and combinations of blocks in the flowchart illustrations and/or block diagrams, can be implemented by computer program instructions.

Various modifications and additions can be made to the exemplary instances discussed without departing from the scope of the disclosed subject matter. For example, while the instances described above refer to particular features, the scope of this disclosure also includes instances having different combinations of features and instances that do not include all of the described features. Accordingly, the scope of the disclosed subject matter is intended to embrace all such alternatives, modifications, and variations as fall within the scope of the claims, together with all equivalents thereof.

We claim:

1. A non-transitory computer-readable storage medium storing instructions, which, when executed by a processor, perform an operation, the operation comprising:

causing plots of beats to be displayed together, including causing the plots of beats to be displayed superimposed on each other, the plots of beats are each associated with a first beat classification, the first beat classification indicated by metadata associated with each beat;

receiving a selection of one of the plots of the beats to identify a selected beat;

creating a subgroup of the beats based on a comparison of the beats associated with the first beat classification relative to the selected beat; and reclassifying the beats in the subgroup to a second beat classification by updating the metadata associated with the beats in the subgroup.

2. The computer-readable storage medium of claim 1, wherein the comparison is based on latent space representations of the beats and the selected beat.

3. The computer-readable storage medium of claim 2, wherein the latent space representations each include 4-16 datapoints for each beat.

4. The computer-readable storage medium of claim 1, the operation further comprising:

calculating respective numerical values for the beats associated with the first classification, wherein the comparison includes comparing the respective numerical values to a threshold.

5. The computer-readable storage medium of claim 4, wherein the respective numerical values are calculated using a Euclidean distance algorithm.

6. The computer-readable storage medium of claim 5, wherein inputs to the Euclidean distance algorithm are values of latent space representations.

7. The computer-readable storage medium of claim 5, wherein the selected beat comprises centroid values for the Euclidean distance algorithm.

8. The computer-readable storage medium of claim 4, the operation further comprising:

receiving a command to increase the threshold to increase the number of beats in the subgroup.

9. The computer-readable storage medium of claim 1, wherein the plots of beats are initially displayed together in a first window on a user interface, the operation further comprising:

extracting the plots of beats associated with the subgroup from the first window; and causing the plots of beats associated with the subgroup to be displayed in a second window.

10. The computer-readable storage medium of claim 1, the operation further comprising: causing the plots of the beats in the subgroup to be displayed in a different color, line type, and/or line weight than the rest of the plots of the beats.

11. The computer-readable storage medium of claim 1, wherein the first beat classification is a ventricular beat, wherein the second beat classification is a normal beat.

12. A system comprising:

a display for displaying a user interface;

one or more processors; and a non-transitory computer-readable storage medium storing instructions, which, when executed, cause the system to perform one or more operations, the one or more operations comprising:

causing plots of beats to be displayed together on the user interface in a first window, including causing the plots of beats to be displayed superimposed on each other, the plots of beats are each associated with a first beat classification, the first beat classification indicated by metadata associated with each beat, receiving, from the user interface, a selection of one of the plots of the beats to identify a selected beat, calculating respective numerical values for the beats, creating a subgroup of the beats based on a comparison of the beats associated with the first beat classification relative to the selected beat, wherein the comparison includes comparing the respective numerical values to a threshold, and causing the plots of beats of the subgroup to be displayed together on the user interface in a second window.

13. The system of claim 12, the one or more operations further comprising reclassifying the beats in the subgroup to a second beat classification.

14. The system of claim 12, wherein the respective numerical values are calculated using a Euclidean distance algorithm.

15. A method comprising:

displaying together plots of beats that are each associated with a first beat classification, including displaying the plots of beats superimposed on each other;

selecting one of the plots of the beats to identify a selected beat;

creating a subgroup of the beats based on a comparison of the beats associated with the first beat classification relative to the selected beat; and reclassifying the beats in the subgroup to a second beat classification.

16. The method of claim 15, wherein the comparison is based on latent space representations of the beats and the selected beat.

17. The method of claim 16, further comprising:

calculating respective numerical values for the beats associated with the first classification, wherein the comparison includes comparing the respective numerical values to a threshold.

18. The method of claim 17, wherein the respective numerical values are calculated using a Euclidean distance algorithm.

* * * * *